(12) United States Patent
Faul et al.

(10) Patent No.: US 8,638,450 B2
(45) Date of Patent: Jan. 28, 2014

(54) METHODS AND SYSTEMS FOR REALIZING REDUCED COMPLEXITY IN THREE-DIMENSIONAL DIGITIZER SYSTEMS

(75) Inventors: Ivan Faul, Boulder, CO (US); Dennis Toms, Estes Park, CO (US)

(73) Assignee: Boulder Innovation Group Inc., Boulder, CO (US)

( * ) Notice: Subject to any disclaimer, the term of this patent is extended or adjusted under 35 U.S.C. 154(b) by 0 days.

(21) Appl. No.: 13/197,599

(22) Filed: Aug. 3, 2011

(65) Prior Publication Data
US 2012/0086953 A1 Apr. 12, 2012

Related U.S. Application Data

(60) Provisional application No. 61/370,720, filed on Aug. 4, 2010.

(51) Int. Cl.
*G01B 11/14* (2006.01)

(52) U.S. Cl.
USPC .......................................................... 356/614

(58) Field of Classification Search
USPC .......................................................... 356/614
See application file for complete search history.

(56) References Cited

U.S. PATENT DOCUMENTS

| 6,608,688 B1 * | 8/2003 | Faul et al. ..................... 356/614 |
| 6,611,344 B1 | 8/2003 | Chuang et al. |
| 6,741,363 B1 | 5/2004 | Kaupert |
| 2004/0150836 A1 | 8/2004 | Kraus |
| 2005/0088529 A1 * | 4/2005 | Geng ........................ 348/207.99 |
| 2009/0220256 A1 * | 9/2009 | Suhara et al. ................... 399/32 |

FOREIGN PATENT DOCUMENTS

| JP | 2004-110184 A | 4/2004 |
| KR | 10-2001-0097765 A | 11/2001 |
| KR | 10-2005-0102751 A | 10/2005 |
| WO | 2005-074653 A2 | 8/2005 |

OTHER PUBLICATIONS

International Search Report and Written Opinion issued in PCT Application No. PCT/US2011/046557, mailed on Feb. 24, 2012.
International Preliminary Report on Patentability issued in International Application PCT/US2012/033466, having a mailing date of Oct. 24, 2013.

* cited by examiner

*Primary Examiner* — Tu Nguyen
(74) *Attorney, Agent, or Firm* — The Marbury Law Group, PLLC

(57) ABSTRACT

A simplified system and method for synchronizing a three dimensional digitizers is disclosed. Various three dimensional digitizers utilize detected light sequences received from a probe as a synchronization signal negating the need for complex synchronization circuitry and communication signals. One embodiment utilizes no transmitted synchronization signal, but relies on embedded, high-stability clocks to maintain synchronization after initial one-time synchronization of the clocks. In this manner the design of the three dimensional digitizer may be simplified.

33 Claims, 4 Drawing Sheets

METHODS AND SYSTEMS FOR REALIZING REDUCED COMPLEXITY IN THREE-DIMENSIONAL DIGITIZER SYSTEMS

RELATED APPLICATIONS

This application claims the benefit of priority to U.S. Provisional Application No. 61/370,720, filed Aug. 4, 2010, the entire contents of which are incorporated herein by reference.

FIELD

The present invention relates generally to three-dimensional digitizers, and more particularly to three-dimensional digitizers with optical sensors.

BACKGROUND

Various systems and methods exist for using optical instruments to measure position in a three-dimensional space. These systems and methods may convert the position measurements into digital form and plot the measurements over time to trace various shapes and forms. For example, these systems may operate as a digitizing pointer held by hand and used to trace structures for reverse-engineering, sizing purposes, medical procedures, or motion tracking.

SUMMARY

The need exists for optical digitizing systems that employ lower-cost probes and trackers, which in some cases can be disposable. In an embodiment, optical digitizing systems and methods utilize a controller having increased capabilities in conjunction with probes and/or trackers which are simplified in order to reduce cost. Increased intelligence and cost in the controller can be tolerated in return for simplified probes and trackers.

With such a simplified probe or tracker, the synchronization that is normally achieved by means of built-in intelligence in the probe or tracker is achieved in some other way, preferably by means of increased intelligence in the controller.

In accordance with one aspect of the invention, systems and methods for determining spatial coordinates include a probe that flashes one or more light emitters autonomously, an optical sensor that receives the flashing of the probe's light emitter(s), and a controller that synchronizes the operation of the sensor system with the light flashes from the probe.

In one embodiment, the controller captures and processes images from the sensor continuously with a frame sequence period approximately equal to the period of the probe's emitter flashing sequence. Synchronization is accomplished by shifting the start of the controller's frame sequence until the image height or intensity of one or more emitters on one or more sensors is maximized. As used herein, the image "height" refers to the maximum pixel value in the image, and the "intensity" refers to the total energy of the image, i.e., the area under the curve of the image. Either metric can be used to determine optimum image capture to maximize the image. The controller then identifies the position of each emitter within the sequence. This is easily done if a gap is left in the probe's flashing sequence (the gap may be used for a background capture frame).

In an alternate embodiment, one of the emitters can be flashed twice to allow the controller to identify that emitter. In the event that switches or buttons are attached to a probe, information on button presses and switch closures can be communicated to the controller by flashing emitters in gaps in the flashing sequence where imaging emitter flashes are not expected. In the absence of any gaps in the flashing sequence the emitter identities can still be determined by analyzing the x, y, z coordinates of each emitter in terms of the probe geometry. In the case of more than one emitter being on at the same time, the known geometry of the probe (emitter pattern) can be used to identify each individual emitter or the probe tip directly.

In a further embodiment, the controller is enhanced by adding a photo sensor of a type that is sensitive to the flashing light emanating from the probe. This is in addition to the photo-sensitive elements, typically charge coupled devices ("CCD"), that are sensitive to the same light and uses it for the actual tracking. The photo sensor detects the light flashes from the probe, which the controller uses to synchronize itself to the probe.

In a further embodiment, the controller is enhanced by adding a photo sensor of a type that is sensitive to light at a different electromagnetic frequency than the light that is emitted in the probe flashing sequence. In this embodiment, the probe includes a transmitter that emits light at this different frequency. This photo transmitter is fired in sync with the flashing imaging emitters to signal the start or any other portion of the flashing sequence.

In a further embodiment, synchronization is achieved by utilizing high stability clocks in both the controller as well as in the probe or tracker. After the clocks have been synchronized at a point in time, they keep running in sync for the duration of the measurement procedure, with the probe flashing the markers at the time expected by the controller.

In a further embodiment a wireless sync signal is sent from the controller to all probes and trackers to signal the start of the marker flashing sequence. The sync sent out from the controller would preferably be of infrared or radio frequency in nature.

In a further embodiment, the controller is reduced in size by utilizing modern highly integrated circuits and is incorporated into the sensor housing. A complete system so constructed can consist of the sensor unit, with built-in controller, and a probe or tracker. The user would only need a computer, laptop or other computing device to display the results or otherwise process the results for use in a software application, such as a computer aided design (CAD) program or custom-designed medical or tracking application.

BRIEF DESCRIPTION OF THE DRAWINGS

The accompanying drawings, which are incorporated herein and constitute part of this specification, illustrate example embodiments of the invention, and together with the general description given above and the detailed description given below, serve to explain the features of the invention.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

The word "exemplary" is used herein to mean "serving as an example, instance, or illustration." Any implementation described herein as "exemplary" is not necessarily to be construed as preferred or advantageous over other implementations.

Existing optical digitizing systems typically include a controller, optical sensors, and a probe or tracker. The controller contains the processing engine and generates signals that are sent to the probe. The signals cause the probe to flash emitters of light in time slots expected by the sensor and controller. The flashing probe is then tracked by the optical sensors. Optical sensor systems typically contain two or more photo sensitive instruments, such as cameras or charge coupled devices ("CCD"). The sensors may receive an image of the emitter's light. The images from each of the sensors may be contrasted. The position of the light may be determined in x, y, z coordinates through mathematical processing of the various emitter images and the related geometry of the sensors and/or the probe that the emitters are attached to.

In some systems, the probe contains passive reflectors, which reflect light coming from timed flashes of a separate emitter controlled by the controller. In some cases, where flashing visible light from an emitter or probe would cause disturbance to human operators, infrared light is used.

Various examples of optical systems used for determining coordinates in three-dimensional space are described in, for example, U.S. Pat. No. 6,608,688 to Faul et al., U.S. Pat. No. 5,923,417 to Leis, and U.S. Pat. No. 5,828,770 to Leis et al., each of which is incorporated by reference in its entirety.

Figure 1:
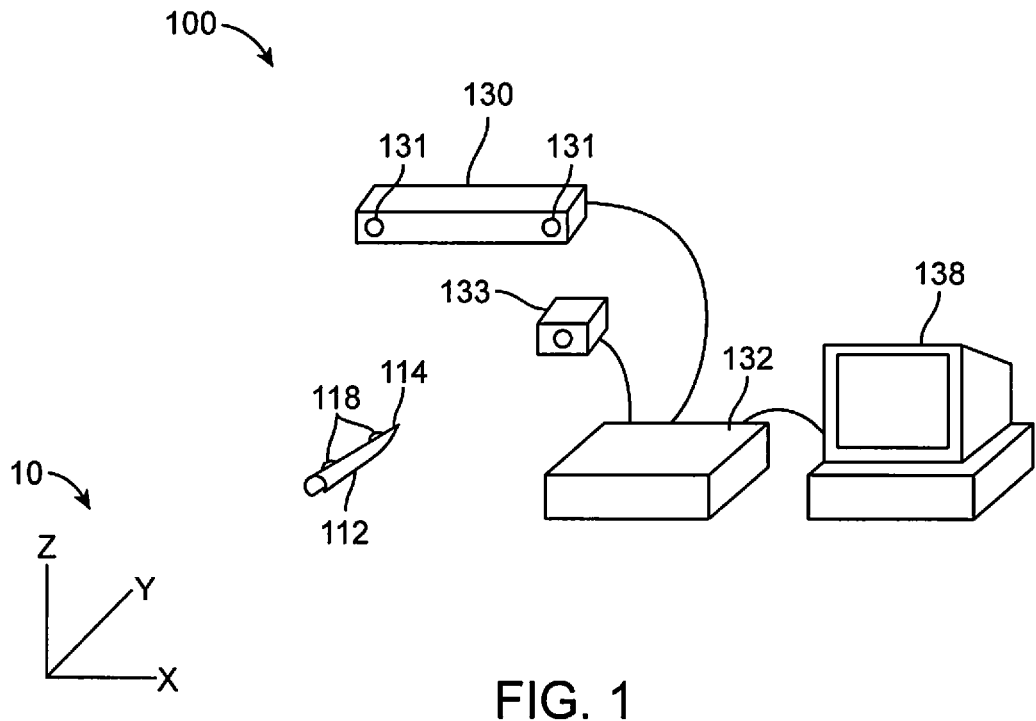
FIG. 1 is a perspective schematic view of an optical system for determining special coordinates.

An embodiment optical system 100 for determining spatial coordinates and orientation in three-dimensional space, indicated at 10, is illustrated in FIG. 1. In general, the system 100 uses optical instruments to measure position (including location and/or orientation) in a three-dimensional space. In exemplary embodiments, the system 100 is a three-dimensional digitizer that converts the position measurements into digital form and plots the measurements over time in order to, for example, trace various shapes or forms or to track the motion of objects, including humans, instruments and such, in 3D space.

The optical system 100 illustrated in FIG. 1 includes a probe 112 having one or more emitters 118 that emit electromagnetic radiation, a sensor system 130 including at least two optical sensors 131, such as cameras or charge coupled devices (CCDs), that are photo-sensitive to the radiation from emitter(s) 118, and a controller 132 that is electronically coupled to and controls the operation of the sensor system 130. A computer 138 is configured to receive input of data from at least one of the controller(s) 132 and the sensor system 130, and from these data, the computer 138 can calculate the x, y, z coordinates of the location of each emitter 118 that appears as a substantial point source of radiation. In some cases, the computer 138 can receive x, y, z and vector data calculated by the controller 132, and use these data for further processing and/or display. In certain embodiments, the computer 138 can use the computed coordinates of each emitter and a known geometry of the probe 112 to compute the location and orientation of the probe, and any point on the probe, such as the probe tip 114. The computer 138 can also determine the unit 3D vector describing the longitudinal direction of the probe (which is one aspect of the orientation of the probe). If more than two non-collinear electromagnetic ray emitters are disposed on the probe, a transverse 3D vector can also be computed to describe the rotational orientation of the probe or its yaw-pitch-and-roll angles.

For clarity, the controller 132 and computer 138 in this embodiment are illustrated as two separate components, although it will be understood that any of the functions described as being performed by the controller 132 could alternatively or in addition be performed by the computer 138, and vice versa. Moreover, in some embodiments, the controller 132 and computer 138 can be combined in a single device.

In certain embodiments, the controller 132 and the sensor system 130 are combined in a single device. The controller 132 can be made highly-compact by utilizing modern highly integrated circuits, for example, and incorporating them into a common housing with the sensor system 130. A complete system so constructed may comprise the sensor system 130, with built-in controller 132, and one or more probe(s) 112 or tracker(s). The probe(s) 112 can be simplified low-cost probe (s), or even disposable probe(s), as described below. The user can utilize a computer 138, which could be a laptop, tablet, or other computing device, to display the results or otherwise process the results for use in a software application, such as a CAD program or custom-designed medical or tracking application.

Figure 2:
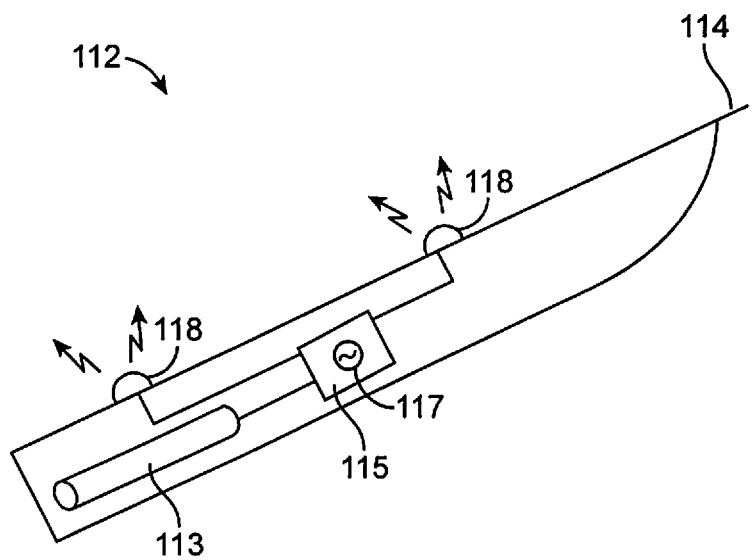
FIG. 2 is a perspective view of a probe having a plurality of emitters.

Three dimensional digitizers enjoy a wide range of uses. In some of these uses, a need exists for a simplified probe. An exemplary embodiment of a probe 114 is illustrated in FIG. 2. The probe 114 includes a plurality of energy emitters 118. The emitters 118 may generally be active light emitting elements, such as light emitting diodes (LEDs), although they may also be passive reflecting elements that emit reflected light from an external light source. The probe 114 further includes a power source 113, which can be a battery, and a pulse generating circuit 115 that causes the emitter(s) 118 to flash light in a particular, generally periodic, sequence. In certain embodiments, the probe 114 flashes its emitters autonomously, meaning that the probe's emitter flash sequence is not determined or controlled by commands from an external control system such as controller 132. In this way, the probe 114 can be greatly simplified relative to conventional probes. In certain embodiments, the probe 114 includes a simplified circuit that includes a power source 113 (e.g., a battery), a straightforward pulse generating circuit 115 that may be as simple as a free-running oscillator 117, and light emitters 118.

The simplified probe 114 of this embodiment does not need to include the advanced electronic circuitry that enables conventional probes of this type to receive and interpret commands from a controller and flash each of its light emitters in precise time-slots prescribed by the controller. A drawback of these conventional probes is that they can be expensive to manufacture. By contrast, the present simplified probe is generally cheaper to produce and easier to replace. These simplified probes can be advantageously used in hazardous applications, for example, where the probe is likely to be damaged. In other embodiments, the probe is used in medical applications or other applications that require a sterile probe. In such applications, the probe can be a disposable probe designed for a single use. The present simplified probe can also be used in low cost consumer applications.

The controller 132 can be configured to detect and synchronize its own control circuitry with the autonomous flashing of the probe 112. Added intelligence to the controller provides the ability for it to seek and synchronize to the probe emitters. Thus embodiments may include a more complex and expensive controller, but the probes become cheaper and simpler. Therefore, various embodiments of an optical system can include multiple probes, disposable probes, and/or multiple disposable probes.

Figure 3:
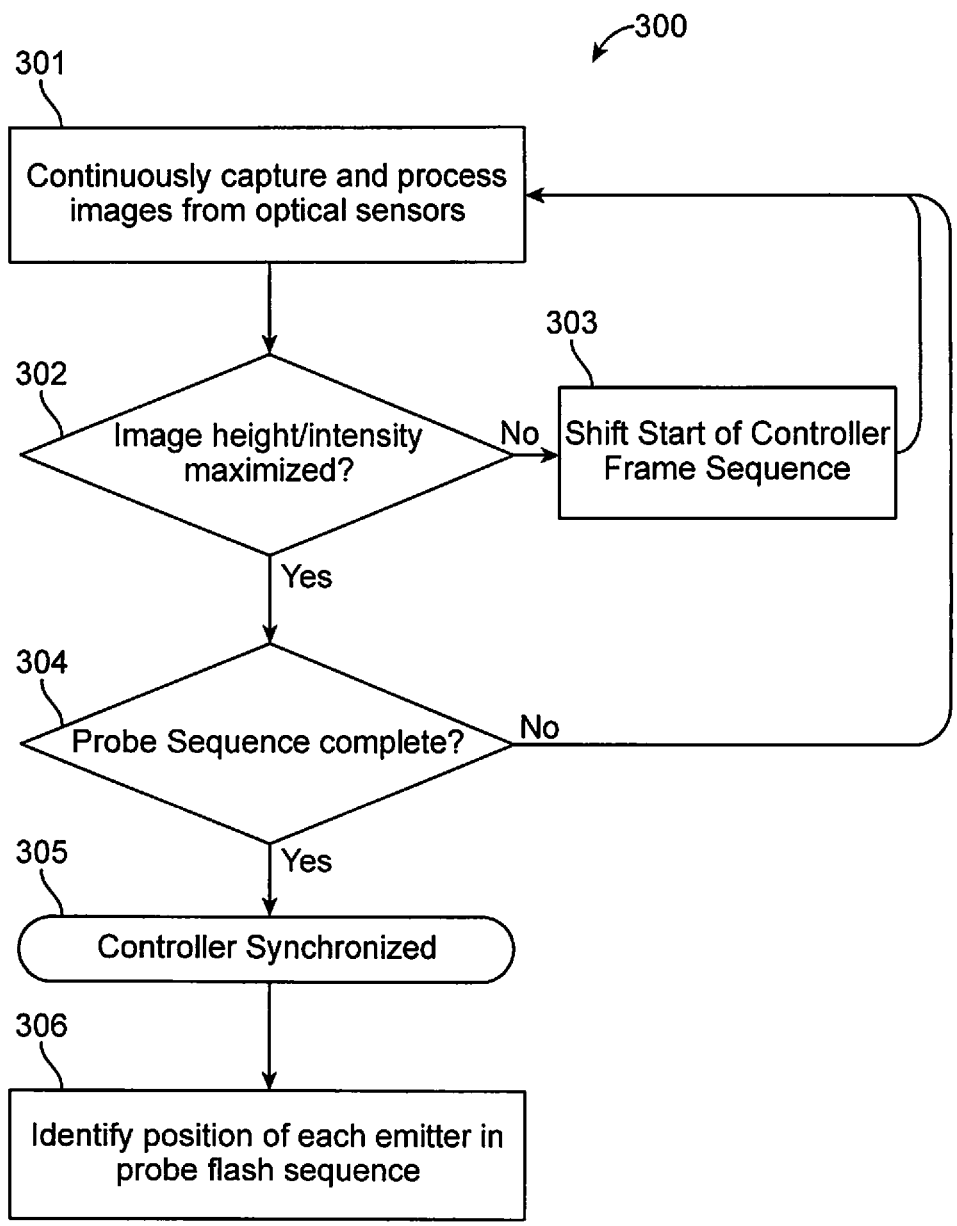
FIG. 3 is a process flow diagram of an example of a method for synchronization of a controller and an autonomously flashing probe.

Controllers may synchronize with an autonomously flashing probe in different ways. In one embodiment of a synchronization method 300, illustrated in the process flow diagram of FIG. 3, the controller captures and processes images from optical sensors, such as cameras or charge coupled devices ("CCD"). At step 301, these images are processed continuously with a frame sequence period approximately equal to the period of the probe's emitter flashing sequence. Synchronization is accomplished by shifting the start of the controller's frame sequence (step 303) and measuring the image height or intensity of one or more emitters on one or more probes. When the image height or intensity is maximized (step 302), the sensor and probe are synchronized (step 305). Each emitter's location in the flash sequence is determined (step 306) based on the start of the sequence. The sequence start can be determined by leaving a gap, during which time no emitter is flashed, at the end of the sequence.

An alternative to leaving a gap in the emitter flash sequence is to flash one emitter twice. Identifying the position of each emitter 306 is facilitated by detecting the double emitter-flash. In the event that switches or buttons are attached to a probe, information on button presses and switch closures can be communicated to the controller by flashing emitters in gaps in the flashing sequence where imaging emitter flashes are not expected. In the absence of any gaps in the flashing sequence the emitter identities can still be determined by analyzing the x, y, z coordinates of each emitter in terms of the probe geometry. In the case of more than one emitter being on at the same time, the known geometry of the probe or emitter pattern may be used to identify each individual emitter or the probe tip directly.

In an embodiment, the optical system 100 can include an additional photo sensor 133 that is coupled to the controller 132, as shown in FIG. 1. The controller 132 uses the additional photo sensor 133 to synchronize with an autonomously-operating probe 112 or emitter 118. In an embodiment, the photo sensor 133 detects a flash of light from emitter 118 and generates a pulse that is received at the controller 132. The pulse is used by the controller 132 to start the optical sensors or CCDs 131 clocking, thus timing the sensors 131 to the flashing of the emitters 118 on the free-running probe 112.

The additional photo sensor 133 can be sensitive to the light flashed by the emitter(s) 118 on probe 112. In an alternative embodiment, the photo sensor 133 is sensitive to light having a different electromagnetic frequency than the light from the probe emitters 118. In this case, the probe 112 includes a transmitter that emits light at this different frequency. The transmitter is fired in sync with the imaging emitters 118 to signal the start or any other portion of the flashing sequence.

The controller 132 and the probe 112 can each include high-stability clock circuitry, so that once the controller 132 and the autonomously-flashing probe 112 are synchronized at one point in time, they will remain synchronized over an extended duration, preferably over the duration of one or more measurement/digitization procedures.

Figure 4:
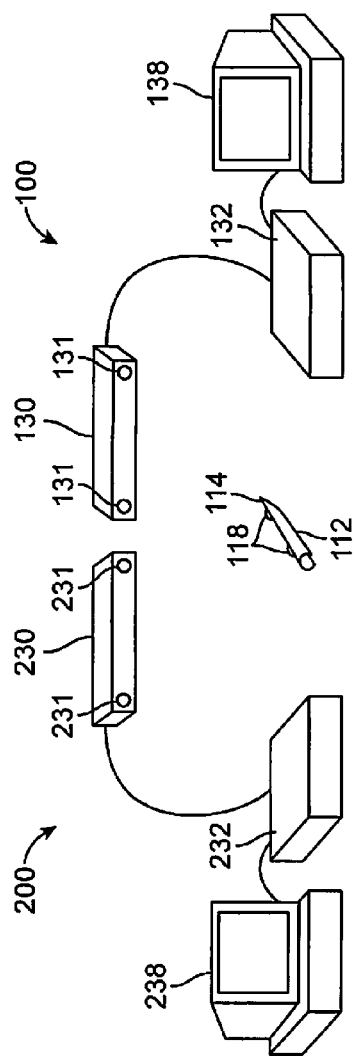
FIG. 4 is a perspective schematic view of an optical system including multiple controllers and optical sensor systems.

Further embodiments may include multiple controllers 132, 232, as shown in FIG. 4. In order to cover measurement volumes larger than what a single controller and associated optical sensors are able to observe, multiple systems 100, 200 can be cascaded to receive signals from the same autonomously flashing probe 112 or probes. These multiple systems 100, 200 may each include a controller 132, 232 and an optical sensor system 130, 230. The respective controllers 132, 232 sync to the same probe 112 using their individual synchronizing circuitry and/or algorithms. This is highly simplified compared to existing systems in which controllers must be synchronized with each other to generate a uniform signal to a probe.

Figure 5:
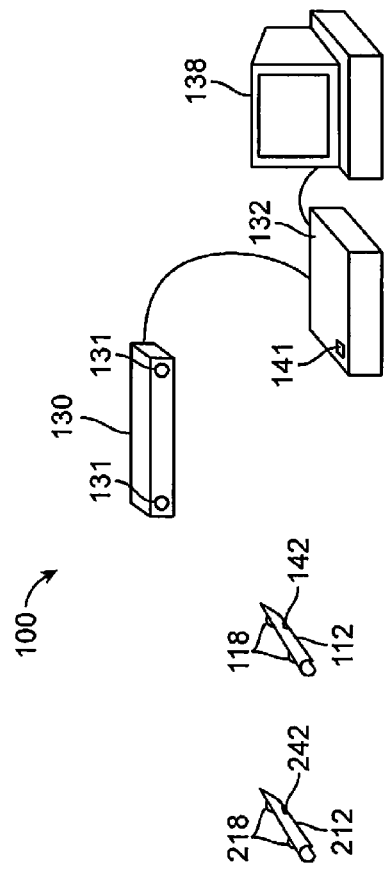
FIG. 5 is a perspective schematic view of an optical system including multiple probes.

Some embodiments may include multiple probes. FIG. 5 illustrates an embodiment in which two probes 112, 212, each having a plurality of emitters 118, 218, are both within the field-of-view of sensor system 130. When more than one probe is used, the controller 132 may have to deal with more than one light flash at the same time. A controller 132 can overcome this problem and synchronize with multiple probes by implementing one or more embodiment methods. In one embodiment, the probes 112, 212 are configured to flash their respective emitters 118, 218 at different flash rates. Thus, for example, the controller 132 would detect images with multiple flashes and images with only one flash, and use these images to identify the respective emitters 118, 218 and synchronize with each of the multiple probes 112, 212 using the different flash rates to distinguish the probes. In another embodiment, the controller 132 includes a transmitter 141 that sends out a periodic sync signal. This signal can be, for example, a radiofrequency or optical signal (e.g., infrared, visible light, etc.) that is received by a receiver 142, 242 on the probe(s) 118, 218. This signal can tell the probes to restart or re-sync their individual, autonomous flashing sequences. In another embodiment, the probes 112, 212 can send short signals to each other (e.g., via radio frequency or optical signaling). In an embodiment, the probes 112, 212 can include receivers/detectors 142, 242 that allow them to receive signals from neighboring probes. In this embodiment, the probes 112, 212 can sync with each other by detecting signals from other probes, including for instance the light flashes of other probes.

In further embodiments, synchronization is achieved by utilizing high stability clocks in both the controller 132 and the probe(s) 112, 212. After the clocks have been synchronized at a point in time, they keep running in sync for the duration of the measurement procedure, so the probes flash the markers at the time expected by the controller.

The embodiments discussed above may be combined in various ways to create further embodiment systems, such as a system with both multiple controllers and multiple disposable probes.

Figure 6:
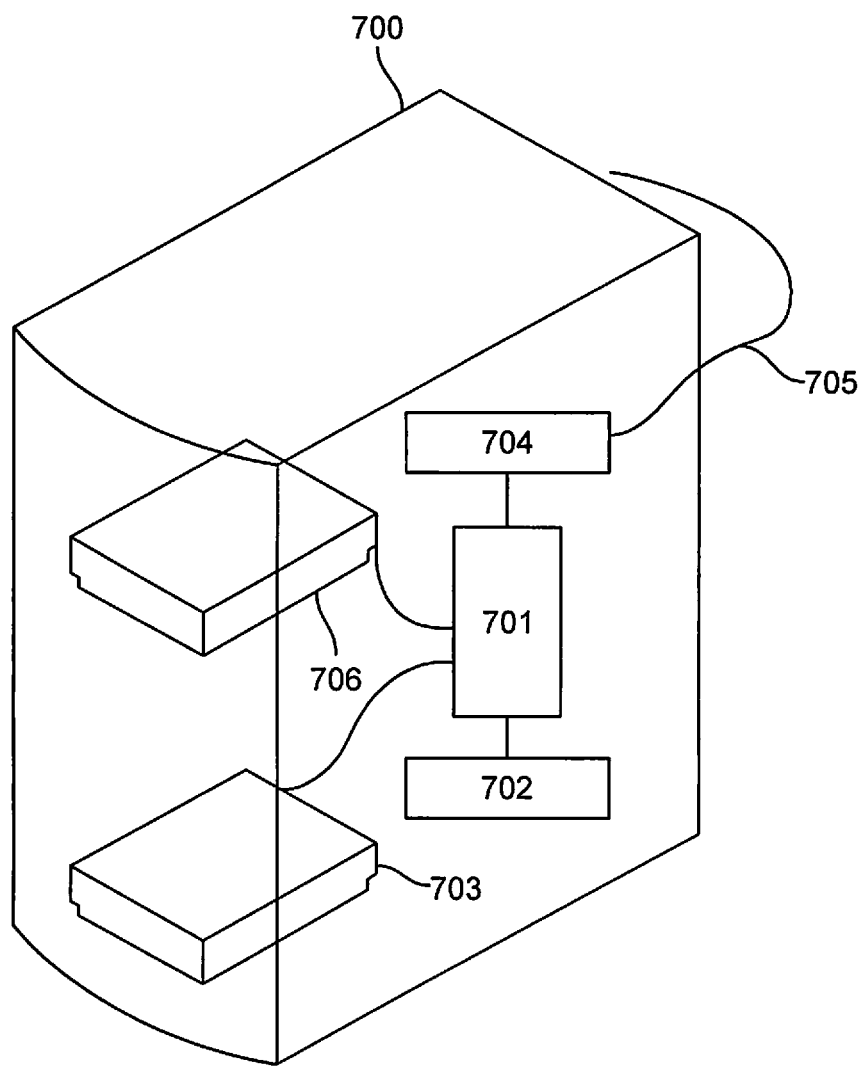
FIG. 6 is a component block diagram of an example computer suitable for use with various embodiments.

A number of the embodiments described above may also be implemented using a variety of commercially available computers, such as the computer 700 illustrated in FIG. 6. Such a computer 700 typically includes a processor 701 coupled to volatile memory 702 and a large capacity nonvolatile memory, such as a disk drive 703. The computer 700 may also include a USB memory device and/or a compact disc (CD) drive 706 coupled to the processor 701. The computer 700 may also include network access ports 704 coupled to the processor 701 for establishing data connections with receiver devices and/or a network 705, such as a local area network for coupling to the receiver devices and controllable elements within a digitizing or tracking system.

Computers and controllers used in the digitizing system for implementing the operations and processes described above for the various embodiments may be configured with computer-executable software instructions to perform the described operations. Such computers may be any conventional general-purposes or special-purpose programmable computer, server or processor. Alternatively, some steps or methods may be performed by circuitry that is specific to a given function.

In one or more exemplary aspects, the functions described may be implemented in hardware, software, firmware, or any combination thereof. If implemented in software, the functions may be stored on or transmitted over as one or more instructions or code on a computer-readable medium. The steps of a method or algorithm disclosed herein may be embodied in a processor-executable software module which may reside on a tangible computer-readable storage medium. Computer-readable storage media may be any available media that may be accessed by a computer. By way of example, and not limitation, such computer-readable media may comprise RAM, ROM, EEPROM, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a machine readable medium and/or computer-readable medium, which may be incorporated into a computer program product.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A system for determining spatial coordinates comprising:
   a probe comprising one or more light emitters configured to produce an autonomously generated sequence of light flashes;
   a sensor system comprising two or more optical sensors; and
   a controller that controls the operation of the sensor system, and is configured to synchronize the operation of the sensor system with the autonomously generated sequence of light flashes from the probe, wherein:
   the operation of the sensor system is associated with a frame sequence according to a first rate, and the autonomously generated sequence of light flashes is according to a second rate approximately equal to the first rate; and
   the controller is configured to synchronize the operation by shifting the frame sequence until a measurement associated with the sensor system indicates that the autonomously generated sequence of light flashes and the frame sequence are synchronized.

2. The system of claim 1, further comprising more than one probe.

3. The system of claim 2, wherein the controller is further configured to synchronize with autonomously generated flash sequences from multiple probes.

4. The system of claim 1, further comprising more than one optical sensor system and controller.

5. The system of claim 4, wherein each of the more than one controllers is configured to synchronize with the autonomously generated sequence of flashes.

6. The system of claim 1, further comprising:
   a photo sensor that detects a light flash from the emitter and generates a pulse that is used by the controller to time the sensor system to the flashing of the at least one emitter on the probe.

7. The system of claim 1, wherein the probe further comprises:
   an auxiliary light emitter configured to operate at a different electromagnetic frequency than the light emitter producing the autonomously generated sequence of light flashes; and
   a photosensor associated with the controller that detects a light flash from the auxiliary emitter and generates a pulse to time the sensor system to the flashing of the auxiliary emitter.

8. The system of claim 1, wherein the probe is a disposable probe.

9. The system of claim 1, wherein the probe further comprises:
   a power source; and
   an oscillator for producing the autonomously generated sequence of light flashes.

10. The system of claim 1, where autonomously generated sequence of light flashes is periodic.

11. The system of claim 10, wherein the probe is configured to include a gap in the autonomously generated sequence during which one or more of the emitters is not flashed, and where the gap indicates to the controller the end of a probe flash sequence or the start of a new probe flash sequence.

12. The system of claim 1, wherein the probe further comprises a receiver for receiving a signal, and wherein the probe is configured to modify the autonomously generated sequence of light flashes in response to the received signal.

13. The system of claim 12, wherein the signal is received from the controller and is one of a radio frequency signal and an optical signal.

14. The system of claim 12, wherein the probe is configured such that in response to the received signal, the probe restarts the autonomously generated sequence of flashes.

15. The system of claim 12, wherein the received signal is from another probe and is one of a radio frequency signal and an optical signal.

16. The system of claim 15, wherein the received signal is a light flash from another probe.

17. The system of claim 1, wherein the probe and the controller both include high stability clocks, and wherein the controller is further configured such that once the controller is synchronized with the autonomously generated sequence of flashes, the controller and probe remain synchronized for the duration of one or more measurement procedures.

18. The system of claim 1, wherein the controller and the sensor system are provided in a common housing.

19. A method for determining spatial coordinates comprising:
   flashing a plurality of light emitters of a probe autonomously;

receiving the autonomous flashing of the plurality of light emitters via an optical sensor; and synchronizing a controller with the autonomous flashing of the plurality of light emitters, wherein;

the optical sensor is associated with a frame sequence according to a first rate, and the autonomous flashing of the plurality of light emitters is according to a second rate approximately equal to the first rate; and the synchronizing the controller comprises shifting the frame sequence until a measurement associated with the optical sensor indicates that the autonomous flashing of the plurality of light emitters and the frame sequence are synchronized.

20. The method of claim 19, wherein the shifting the frame sequence until the optical sensor indicates further comprises:
detecting an intensity of the autonomous flashing of the polarity of light emitters; and
shifting the frame sequence a maximum value of the intensity is detected.

21. The method of claim 19, further comprising:
flashing the plurality of light emitters in an autonomous flash sequence; and
determining the position of each of the plurality of light emitters in the autonomous flash sequence to synchronize the controller with the light emitters.

22. The method of claim 19, further comprising:
continuously capturing and processing images of the flashing of the plurality of light emitters until the controller is synchronized with the flashing of the light emitter.

23. The method of claim 19, further comprising:
flashing an emitter of the plurality of light emitters at least twice during a period of a probe flash sequence; and
detecting the multiple flashes to identify the emitter within the flash sequence.

24. The method of claim 19, further comprising:
detecting a gap in a flash sequence in which the emitter is not flashed; and
using the gap to determine an end or a start of a probe flash sequence.

25. The method of claim 19, further comprising:
receiving flashes from multiple light emitters simultaneously via an optical sensor; and
differentiating between multiple light emitters to synchronize the controller with the flashing multiple light emitters from at least one probe.

26. The method of claim 19, further comprising:
flashing multiple emitters from at least two probes autonomously;
receiving the autonomous flashing of the multiple emitters via an optical sensor; and
synchronizing the controller with the autonomous flashing of the multiple emitters from the at least two probes.

27. The method of claim 26, further comprising:
flashing at least one emitter from a first probe of the at least two probes at a first flash rate different from a second flash rate of the flashing of at least one emitter from a second probe of the at least two probes.

28. The method of claim 26, further comprising:
transmitting a signal to at least one of the at least two probes;
receiving the signal in the at least one of the as least two probes; and
modifying the autonomous flashing of the light emitter in response to the signal.

29. The method of claim 28, wherein the signal is transmitted from a transmitter associated with the controller.

30. The method of claim 28, wherein the signal is transmitted between the at least two probes.

31. The method of claim 19, further comprising:
receiving the autonomous flashing of the plurality of light emitters via a second optical sensor associated with a second controller; and
synchronizing the second controller with a flashing sequence associated with the autonomous flashing of the plurality of light emitters.

32. The method of claim 19, wherein the probe is disposable.

33. The method of claim 19, further comprising:
detecting an image in the optical sensor, the image associated with a body in the field of the optical sensor; and
shifting a start of a controller frame sequence so as to start the synchronizing in response to detecting a maximum size of the image.

* * * * *